US00PP20972P2

(12) United States Plant Patent
Zaiger et al.

(10) Patent No.: US PP20,972 P2
(45) Date of Patent: May 4, 2010

(54) PLUM TREE NAME 'FALLETTE'

(50) Latin Name: *Prunus salicina*
Varietal Denomination: Fallette

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/321,746

(22) Filed: Jan. 26, 2009

(51) Int. Cl.
*A01H 5/00* (2006.01)

(52) U.S. Cl. ..... Plt./184

(58) Field of Classification Search ..... Plt./184
See application file for complete search history.

*Primary Examiner*—Kent L Bell

(57) ABSTRACT

A new and distinct variety of plum tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous upright growth.
2. Fruit with attractive red skin color.
3. Fruit ripening in the very late maturity season.
4. Fruit having a good balance between acid and sugar with an average Brix of 17.2°.
5. Heavy and regular production of fruit.

1 Drawing Sheet

Botanical classification: *Prunus salicina.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of plum tree was originated and asexually reproduced by us in our experimental orchard located near Modesto, Stanislaus County, Calif.

PRIOR VARIETIES

Among the existing varieties of plum trees, which are known to us, and mentioned herein, are 'Friar' Plum (non-patented), and 'King David' Plum (non-patented).

STATEMENT REGARDING FEDERALLY SPONSORED RESEARCH AND DEVELOPMENT

Not applicable.

ORIGIN OF THE VARIETY

The new and distinct variety of plum tree (*Prunus salicina*) was developed by us in our experimental orchard located near Modesto, Calif. It originated from seed of an open pollinated proprietary seedling with field identification number '297LC176', this seedling was developed by us from crosses of 'Friar' Plum (non-patented) and 'King David' Plum (non-patented). The pollen parent is unknown. A large group of these open pollinated seedlings were planted and grown on their own root system. Under close observation, one such seedling, which is the present variety exhibited desirable tree and fruit characteristics and in 1993 was selected for asexual propagation and commercialization.

ASEXUAL REPRODUCTION OF THE VARIETY

Asexual reproduction of the new and distinct variety of plum tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of plum tree is of large size, vigorous, upright growth and a productive and regular bearer of large, attractive red skin fruit, with good flavor and eating quality and maturing in the late maturity season. The fruit is further characterized by having firm yellow flesh, a good balance between acid and sugar, with an average Brix of 17.2° . In comparison to its proprietary seed parent (297LC176), the fruit of the new variety is more even in ripening throughout the tree, larger in size, having an attractive red skin color compared to light blue, more round in shape and is approximately 35 days later in maturity.

PHOTOGRAPH OF THE VARIETY

The accompanying color photographic illustration shows typical specimens of the foliage and fruit of the present new plum variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of plum tree, its flowers, foliage and fruit, as based on observations of 10 year old specimens grown near Modesto, Calif., with color in accordance with Munsell Book of Color.

Tree:

*Size.*—Large. Pruned to approximately 3 to 3.5 meters in height for economical harvesting of fruit. Average spread approximately 3 meters.

*Vigor.*—Vigorous, growth the first growing season of 1.5 to 2 meters, varies with fertility, type of soil and climatic conditions.

*Form.*—Upright, usually pruned to vase shape.

*Branching habit.*—Upright, crotch angle approximately 35°, increases with heavy production.

*Productivity.*—Productive, thinning and spacing of fruit necessary for desired market size.

*Bearer.*—Regular, adequate fruit set 8 consecutive years. No alternate bearing observed.

*Fertility.*—Self sterile, pollinator required.

*Density.*—Medium dense, usually pruned to vase shape, improves new spur growth and enhances fruit color.

*Hardiness.*—Hardy in all stone fruit growing areas of California. Tree grown in USDA Hardiness Zone 9. Winter chilling requirement approximately 900 hours at or below 45° F.

Trunk:

*Size.*—Medium. Average circumference 70.2 cm at 25.4 cm above ground on a 10 year old tree.

*Stocky.*—Medium.

*Texture.*—Medium shaggy, increases with age of growth.

*Color.*—Varies from 10YR 4/2 to 2.5Y 3/2.

Branches:

*Size.*—Medium. Average circumference 18.0 cm, measured at 1.1 meters above ground. Average crotch angle 35°, increases with heavy crop load.

*Surface texture.*—New growth relatively smooth. Mature growth moderately rough, roughness increases with age.

*Lenticels.*—Average number 31 in a 25.8 sq cm surface. Size — large. Average length 4.2 mm. Average width 1.8 mm. Color varies from 7.5YR 4/6 to 7.5YR 4/8.

*Color.*—New growth 5GY 6/6 to 5GY 5/8. Old growth 10YR 3/6 to 2.5Y 3/4, varies with age of growth.

Leaves:

*Size.*—Medium to large. Average length 124.2 mm, varies from 100.9 mm to 147.1 mm. Average width 57.0 mm, varies from 46.9 mm to 67.6 mm.

*Form.*—Elliptical.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins, glabrous. Lower surface relatively smooth except for small ridges created by midrib and pinnate venation, glabrous.

*Petiole.*—Size — small. Average length 14.0 mm. Average width 1.7 mm. Color varies from 5GY 4/6 to 5GY 6/6. Longitudinally grooved. Surface — very short pubescence.

*Glands.*—Globose. Size — medium. Average length 0.8 mm. Average diameter 0.5 mm. Average number 3, varies from 2 to 4. Located primarily on base of leaf blade and upper portion of petiole. Color varies from 5GY 6/6 to 5GY 5/6.

*Color.*—Upper surface varies from 5GY 4/8 to 2.5GY 2/2. Lower surface varies from 5GY 5/4 to 5GY 4/4. Midvein color varies from 5GY 7/2 to 5GY 6/4.

Flower buds:

*Size.*—Small to medium. Average length 8.6 mm. Average diameter 5.7 mm.

*Hardiness.*—Hardy with respect to California winters.

*Form.*—Conical, becoming elongated before opening.

*Pedicel.*—Average length 10.1 mm. Average width 0.6 mm. Color varies from 10Y 6/6 to 2.5GY 6/6.

*Color.*—N 9.5/ (white).

*Number of buds per spur.*—Average number 7, varies from 5 to 10.

Flowers:

*Blooming period.*—Date of First Bloom Feb. 26, 2008. Date of Petal Fall Mar. 7, 2008, varies slightly with climatic conditions.

*Size.*—Small. Average height 10.3 mm. Average diameter 17.4 mm.

*Petals.*—Normally 5, alternately arranged to sepals. Size — small. Average length 8.5 mm. Average width 6.4 mm. Form — orbicular, narrows at point of attachment. Both upper and lower surfaces glabrous. Margin — sinuate. Color — N 9.5/ (white).

*Sepals.*—Normally 5, alternately arranged to petals. Size — small. Average length 3.8 mm. Average width 2.5 mm. Shape — triangular. Margin — entire. Both upper and lower surfaces glabrous. Color — upper surface 2.5GY 6/6 to 5GY 5/6. Lower surface 2.5GY 5/6 to 5GY 5/6.

*Stamens.*—Number — average 25 per flower. Average filament length 6.4 mm. Filament color N 9.5/ (white). Anther color varies from 5Y 7/10 to 7.5Y 8/10.

*Pollen.*—Self-sterile, pollinator required. Color varies from 5Y 7/12 to 7.5Y 7/12.

*Pistil.*—Normally one. Surface — glabrous. Average length 6.9 mm. Position of stigma approximately 2.4 mm below anthers. Color varies from 10Y 8/6 to 2.5GY 8/6.

*Fragrance.*—Moderate aroma.

*Number flowers per flower bud.*—Average number 2, varies from 1 to 3.

*Pedicel.*—Average length 12.6 mm. Average width 0.6 mm. Surface — glabrous. Color 2.5GY 6/8.

*Color.*—N 9.5/ (white).

Fruit:

*Maturity when described.*—Firm ripe.

*Date of first picking.*—Oct. 28, 2008.

*Date of last picking.*—Nov. 5, 2008, varies slightly with climatic conditions.

*Size.*—Large. Average diameter axially 66.2 mm. Average transversely in suture plane 61.9 mm. Average weight 167.6 grams, varies slightly with fertility of the soil, amount of thinning and climatic conditions.

*Form.*—Globose, to slightly elongated.

*Suture.*—Very slightly lipped, nearly smooth, extends from base to apex.
*Ventral surface.*—Very slightly lipped.
*Apex.*—Rounded to slightly retuse.
*Base.*—Rounded to slightly retuse.
*Cavity.*—Rounded to slightly elongated in suture plane. Average depth 2.5 mm. Average diameter 6.3 mm.

Stem:
*Size.*—Large. Average length 18.0 mm. Average diameter 2.5 mm.
*Color.*—Varies from 5YR 3/6 to 7.5YR 3/6.

Flesh:
*Ripens.*—Evenly.
*Texture.*—Firm, meaty.
*Fibers.*—Few, small, tender.
*Firmness.*—Very firm, holds firm on tree 10 to 14 days after maturity, shipping ripe.
*Aroma.*—Moderate.
*Amydgalin.*—Undetected.
*Eating quality.*—Good.
*Flavor.*—Good, a good balance between acid and sugar.
*Juice.*—Moderate, enhances flavor.
*Brix.*—Average 17.2°, varies slightly with amount of fruit per tree and climatic conditions.
*Color.*—Yellow, varies from 5Y 6/6 to 5Y 7/6.
*Pit cavity.*—Average length 26.1 mm. Average width 19.7 mm. Average depth 6.1 mm. Color varies from 10YR 5/8 to 2.5Y 6/8.

Skin:
*Thickness.*—Medium.
*Surface.*—Very slightly waffled, nearly smooth.
*Bloom.*—Moderate amount, nearly covered.
*Tendency to crack.*—None.
*Color.*—Ground color varies from 2.5Y 8.5/4 to 5Y 8/4. Overspread with 2.5R 2/2 to 5R 2/6. Some fruit with very small, randomly spaced areas of ground color exposed to give a speckling pattern to skin surface areas.
*Tenacity.*—Tenacious to flesh.
*Astringency.*—Undetected.

Stone:
*Type.*—Clingstone.
*Size.*—Medium to large. Average length 25.3 mm. Average width 19.1 mm. Average thickness 11.4 mm.
*Form.*—Ovoid.
*Base.*—Usually flat, some stones rounded.
*Apex.*—Slightly pointed. Average length 0.7 mm.
*Surface.*—Slightly pitted throughout, one shallow groove on each side of suture, extending from base to apex.
*Sides.*—Unequal, one side extending further from suture plane.
*Ridges.*—Small, narrow ridges extending from base toward apex.
*Tendency to split.*—None.
*Color.*—Varies from 7.5YR 4/6 to 10YR 5/8 when dry.

Kernel:
*Size.*—Small to medium. Average length 15.3 mm. Average width 10.7 mm. Average depth 5.9 mm.
*Shape.*—Ovoid.
*Viability.*—Viable, complete embryo development.
*Skin.*—Color varies from 7.5YR 4/6 to 10YR 4/6.

Use:
*Dessert.*—Market — local and long distance.

Keeping quality: Good, held firm in cold storage 14 days at 38° to 42° F. without internal breakdown of flesh, appreciable loss of flavor or loss of attractive skin color.

Shipping quality: Good, minimal flesh bruising or skin scarring during picking, packing or shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of plum tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of plum tree (*Prunus salicina*), substantially as illustrated and described.

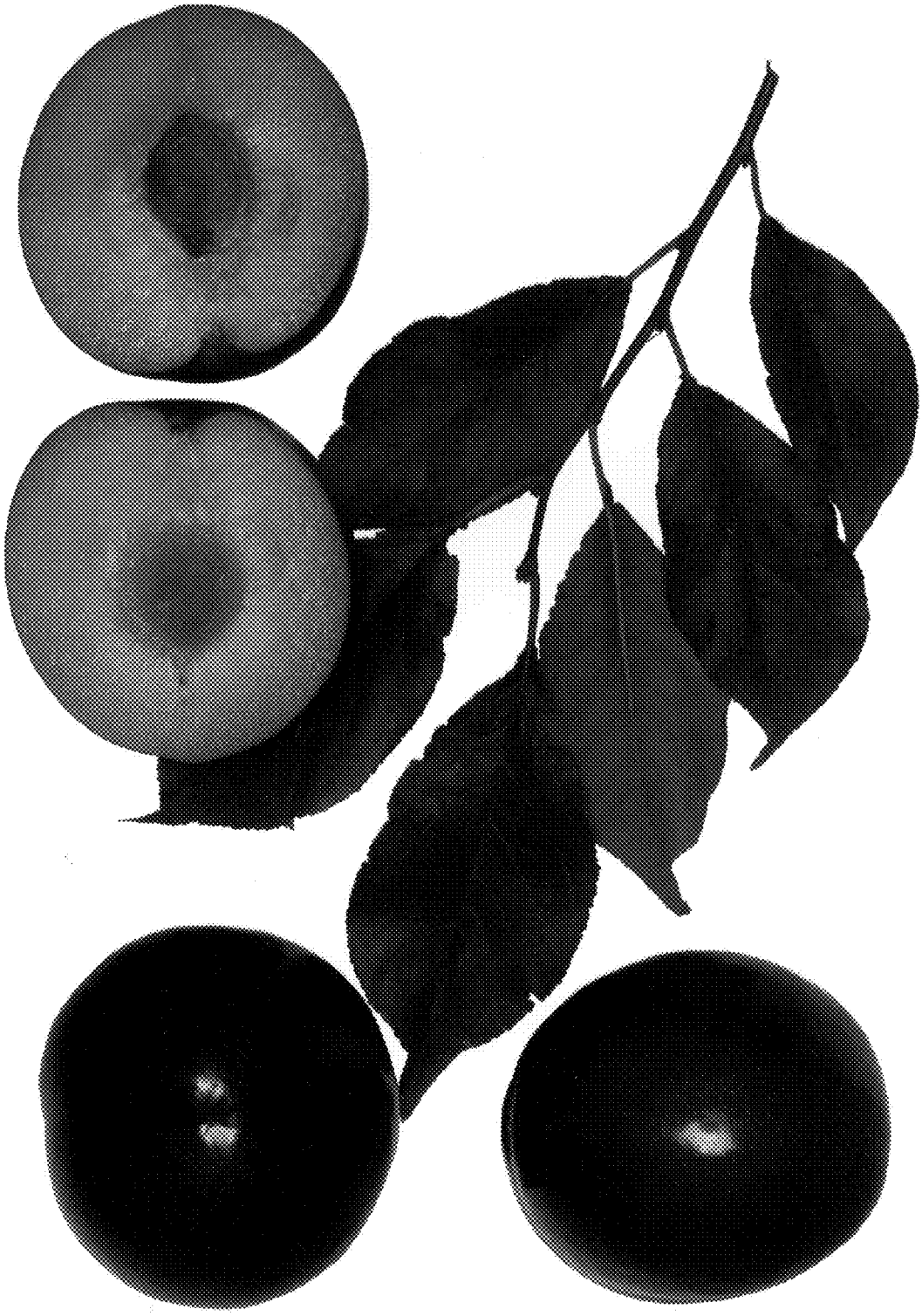

* * * * *